United States Patent

[19]

Cho

[11] 4,052,615

[45] Oct. 4, 1977

[54] SPHERICAL CAVITY METHOD AND APPARATUS FOR MEASURING A SHEET MATERIAL PROPERTY USING INFRARED RADIATION

[75] Inventor: Boong Youn Cho, Columbus, Ohio

[73] Assignee: Industrial Nucleonics Corporation, Columbus, Ohio

[21] Appl. No.: 710,026

[22] Filed: July 30, 1976

[51] Int. Cl.$^2$ ............................................. G01N 21/30
[52] U.S. Cl. ................................... 250/341; 250/338; 250/340
[58] Field of Search ................ 250/338, 339, 340, 341, 250/353

[56] References Cited

U.S. PATENT DOCUMENTS

| | | | |
|---|---|---|---|
| 3,266,313 | 8/1966 | Litterst | 250/338 X |
| 3,319,071 | 5/1967 | Werth et al. | 250/339 |
| 3,551,678 | 12/1970 | Mitchell | 250/341 |

Primary Examiner—Archie R. Borchelt
Attorney, Agent, or Firm—C. Henry Peterson

[57] ABSTRACT

A property such as moisture content in a sheet of material such as paper that both absorbs and strongly scatters infrared radiation is measured by passing the sheet through the central region of a substantially spherical cavity formed between a pair of concave mirror-surfaced, specularly reflecting bodies that are spaced apart to form a pass gap of sufficient width to allow substantially free movement of the sheet therethrough while substantially enclosing a first portion of the sheet on both sides. A spot of infrared radiation is projected onto one side of the sheet in the center of the cavity to illuminate a second portion of the sheet included within and substantially smaller than the enclosed first portion. Thus infrared radiation scattered or transmitted by the second portion is reflected from the mirror-surfaced bodies and directed back to the second portion substantially within the area of the sheet defined by the spot. The relative sizes of the first and second portions in relation to the width of the pass gap determine the relative quantities of radiation being retained in the cavity and escaping through the pass gap. On the opposite side of the sheet relative quantities of both the projected radiation transmitted by the sheet and radiation reflected from the reflective bodies are detected so as to produce an output response indicative of the measured property. The relative quantities of the retained and escaping radiation and the detected transmitted and reflected radiation are selected to make the output response substantially independent of changes in other properties affecting the scattering power of the sheet material, such as the bone-dry weight or composition of paper.

14 Claims, 3 Drawing Figures

SPHERICAL CAVITY METHOD AND APPARATUS FOR MEASURING A SHEET MATERIAL PROPERTY USING INFRARED RADIATION

This invention relates to methods and apparatus utilizing infrared radiation for measuring the properties of sheet materials such as paper that both absorb and strongly scatter the radiation. More particularly it relates to such methods and apparatus for measuring one or more properties of interest while minimizing errors resulting from changes in other properties affecting the scattering power of the sheet.

The invention will be described and illustrated in connection with design and functioning of apparatus for measuring the moisture content of medium-weight and light-weight paper during its continuous production by a paper-making machine. A typical embodiment of the invention is in a tissue paper moisture guage.

In a typical infrared paper moisture gauge, radiations of two different wavelengths are passed through the paper and detected separately, either by time-sharing the use of a single detector or by using separate detectors. The instrument determines the moisture content as a function of the ratio of the separately detected signals. This technique provides common-mode cancellation of the effects of many extraneous variables to an adequate degree. Some of the effects of variations in scattering power, however, are substantially uncompensated.

The scattering power of a sheet material is expressed as the product SX, where S is the scattering coefficient of the material and X is the thickness of the sheet. The coefficient S is determined by the number, kind and arrangement of scattering bodies in a unit volume of the material and hence is determined by the material composition. The thickness X determines the number of unit volumes of material encountered by the radiation beam in a single pass through the material.

One of the effects of scattering is to cause radiation which would otherwise be detected to change direction in such a way that its effect does not register on the detector. For example, some radiation may be scattered from a region near the surface of the material on the side next to the radiation source so that the radiation does not pass through the material to the detector side. Some radiation which does pass through the material may be diverted so as to miss the detector and thereby fail to influence its output. Compensation for this effect has been achieved by the use of integrating spheres or other expedients for collecting the lost radiation. The use of the dual wavelength technique also provides effective compensation, since both wavelengths are scattered about equally.

Another effect of scattering is to cause the radiation to follow a zigzag path through the material and thereby to increase the effective path length for the radiation passing through the material. This effect cannot be compensated for simply by collecting lost radiation. Likewise it cannot be compensated for by the use of dual wavelengths. The effective path length for the reference wavelength may be increased by the scattering to the same extent as the effective path length of the measuring or absorption wavelength, but the resulting fractional increase in the amount of radiation absorbed will be quite different. The measuring wavelength or absorption wavelength if chosen because it is selectively absorbed by certain molecules in the material, such as water molecules in moist paper, while the reference wavelength is not. Hence the two wavelengths of radiation are attenuated in their passage through the material according to two significantly different functions of effective path length.

Attempts have been made to compensate for the latter effect of scattering by the use of fixed artificial scatters such as opal glass or quartz placed next to the material to simulate a maximum degree of scattering even though the amount of scattering which takes place in the material itself is variable and may be small. In some cases this expedient has been supplanted or supplemented by the use of reflectors in an attempt to increase the sensitivity, as by forming an optical cavity. Where sheets of scattering material such as paper are measured, these expedients may not in fact result in increased sensitivity even with the use of the optical cavity. Unless the sample is thin and the reflectors are placed tightly against the sample there is a rapid leakage of radiation through the spacing between the sheet and the reflectors which degrades the effectiveness of the cavity.

Pinching of the sheet to minimize the leakage is of course unacceptable for on-line measurement of moving sheets. To obtain some of the effect of multiple interactions in spite of rapid leakage, some sheet gauges have employed means to prevent the detector from receiving source radiation transmitted directly through the sheet, for example, by offsetting the source and detector apertures. This expedient is inefficient in the use of radiation and can be expected to result in low signal-to-noise ratios. Moreover the effective measured area of the sheet is undefinable for such purposes as calibration or profile and variance analysis since it depends on the thickness of the sheet.

In accordance with the present invention there are provided methods and means for measuring a property such as moisture content in a sheet material such as paper that both absorbs and strongly scatters infrared radiation, comprising the steps of, and apparatus for, passing the sheet through the central region of a substantially spherical cavity formed between a pair of concave mirror-surfaced, specularly reflecting bodies that are spaced apart to form a pass gap of sufficient width to allow essentially free movement of the sheet therethrough while substantially enclosing a first portion of the sheet on both sides, projecting onto one side of the sheet in the center of the cavity a spot of infrared radiation to illuminate a second portion of the sheet included within and substantially smaller than the enclosed first portion so that infrared radiation scattered or transmitted by the second portion will be reflected from the mirror-surfaced bodies and directed back to the second portion substantially within the area of the sheet defined by the spot, the relative sizes of the first and second portions in relation to the width of the pass gap determining the relative quantities of radiation being retained in the cavity and escaping through the pass gap, and detecting on the opposite side of the sheet relative quantities of both the projected radiation transmitted by the sheet and radiation reflected from the reflective bodies so as to produce an output response indicative of said property, said relative quantities of retained and escaping radiation and detected transmitted and reflected radiation being selected to make said response substantially independent of changes in another property affecting the scattering power of the sheet material, such as bone-dry weight or composition of paper. The criteria for, and the manner of selecting the relative quantities and sizes, together with typical and effectively operable values, according to the invention, are described in more detail hereinafter.

The objects of the invention are to provide an improved method and apparatus utilizing infrared radiation for measuring a property of a sheet of material, such as moisture content in light and medium-weight paper, with increased independence of changes in another property, such as bone-dry weight or composition, which affects the scattering power of the sheet; to provide such a method and apparatus that allows free and unrestricted movement of the sheet undergoing measurement, and to provide such a method and apparatus wherein the measured area of the sheet is substantially constant and distinctly defined.

Other objects and advantages of the invention will become apparent in the following detailed description of a typical embodiment, taken in conjunction with the appended drawings, in which.

Figure 1:
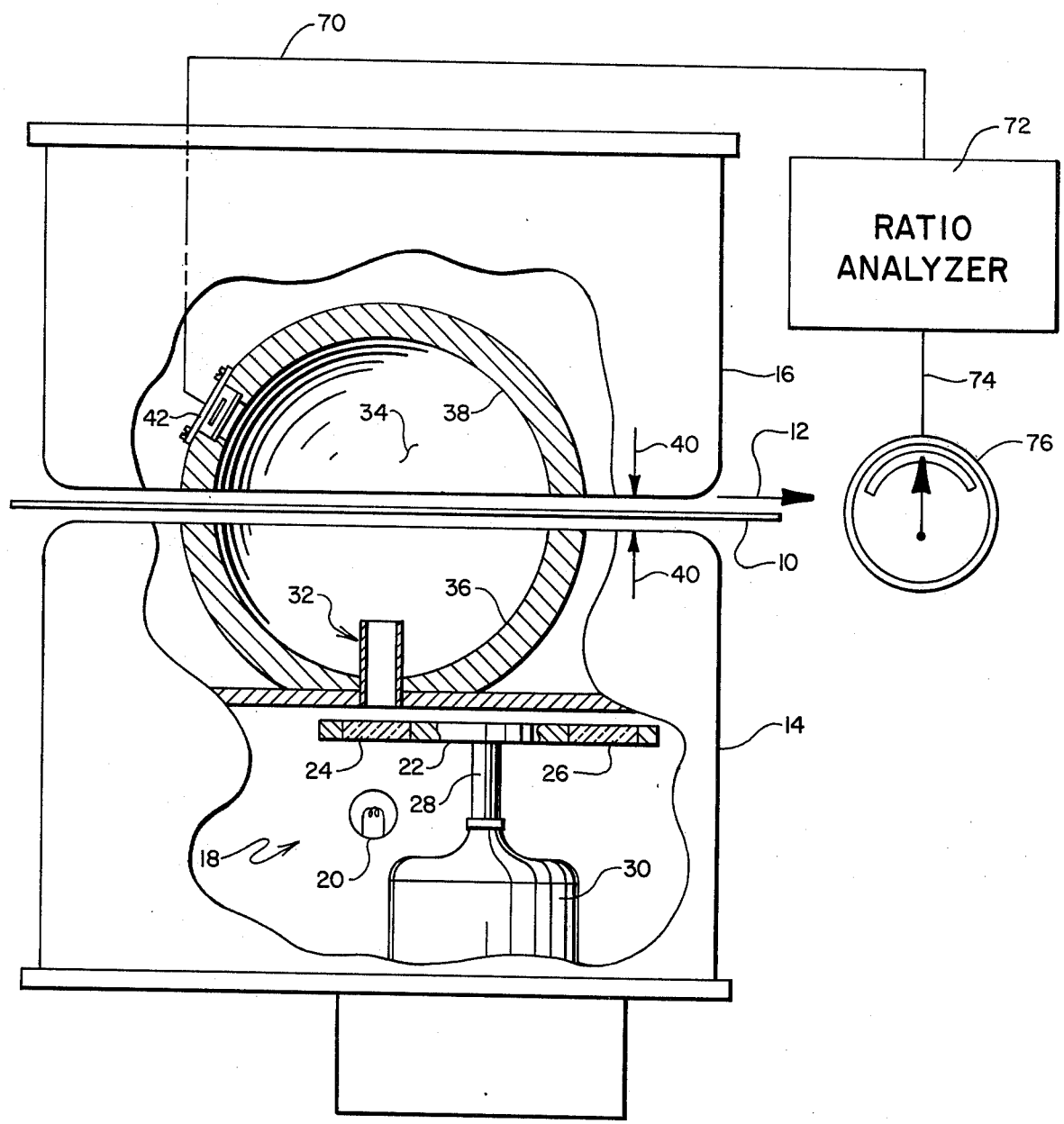
FIG. 1 is a generally schematic, partially sectional view of a measuring instrument including radiation source and detector heads for measuring a property of a sheet such as tissue paper in accordance with the present invention.

Referring to FIG. 1, the numeral 10 indicates the edge view of a medium-weight or light-weight sheet of paper such as tissue paper produced by a tissue paper-making apparatus. The paper will normally be traveling, as indicated by the arrow 12, say, from the calender stack to the windup. Typically, a signal from the measuring apparatus herein disclosed may be used to automatically control or regulate a property of the paper such as its moisture content, bone-dry basis weight or composition by controlling an adjustable parameter of the paper-making machine.

The numeral 14 designates the outline of an infrared radiation source housing and the numeral 16 designates the outline of an infrared radiation detector housing. These are conventional housings, typically mounted on a conventional traversing structure (not shown), which allows the source and detector housings 14 and 16 to traverse back and forth across the width of the traveling sheet 10, in order to gauge the measured sheet property at any point across the width.

Within source housing 14 is a conventional radiation source arrangement indicated generally by the numeral 18. The radiation source arrangement typically includes means for generating first and second infrared radiations having wavelengths selected so that one of the radiations is subject to greater absorption in the material of sheet 10 than the other radiation. Arrangements can be made to generate, or at least to effectively use, radiations in more than two wavelength regions, for example, if both bone-dry weight and moisture are to be measured.

The source arrangement shown includes a conventional lamp 20 and a conventional chopper and filter system. It includes a chopper disc 22 having mounted therein a pair of filters 24 and 26. The chopper disc 22 is driven through shaft 28 by a synchronous motor 30. As motor 30 rotates disc 22, filters 24 and 26 are alternately positioned between lamp 20 and a "light pipe" 32. The filters 24 and 26 are thus enabled to send through light pipe 32 time-alternating infrared radiations of effectively different wavelengths. With specific reference to a moisture gauge, filter 24 selects and passes to light pipe 32 an infrared radiation in a band of "absorption" wavelengths which are subject to molecular resonance absorption by the water in the sheet 10. The radiation selected and passed to light pipe 32 by filter 26 is a reference wavelength which is not subject to such selective absorption by the water molecules in the sheet.

The sheet 10 is passed through the central region, typically the center, of a substantially spherical cavity 34 formed between a pair of concave mirror-surfaced, specularly reflecting bodies 36 and 38. Bodies 36 and 38 are spaced apart to form a pass gap 40 of sufficient width to allow substantially free movement of the sheet 10 therethrough. The bodies 36 and 38 typically have a hemispherical curvature on the inside where the mirror surface is formed. To accommodate the pass gap, a frustum may be "cut" from the base of each hemisphere. To compensate for the effects of sheet flutter and/or like departures from ideal geometry, some departure from a perfect spherical shape may be desirable or necessary. For example, the hemispherical bodies 36 and 38 may be moved farther apart so that the shape of the cavity 34 becomes prolate, When mounted in place, the hemispheres substantially enclose a first portion of the sheet 10 on both sides. The enclosed portion is a circle having substantially the same diameter as the spherical cavity 34.

Light pipe 32 projects onto one side of the sheet 10 (the bottom side as shown) in the center of the cavity 34 a spot of infrared radiation which illuminates a second portion of the sheet. The second portion of the sheet is included within and is substantially smaller than the enclosed first portion. The light pipe 32 is a hollow tube with a shiny metallic surface on inside. Because of the substantial length of the tube and its distances from the radiation source 20 and sheet 10, the spot of radiation projected onto the sheet has about the same diameter as the inside of the tube.

In one embodiment of the invention which has been constructed, the spherical cavity 34 has an inside diameter of $4\frac{3}{8}$ inch and the light pipe 32 had an inside diameter of $\frac{1}{2}$ inch. The light pipe extended into the cavity a distance of 3/4 inch. The pass gap 40 was $\frac{1}{2}$ inch.

This embodiment was constructed as a modification of an existing source and detector head arrangement of the general type disclosed in the copending application of Paul Williams et al. Ser. No. 673,534, filed Apr. 5, 1976 for MEASURING SYSTEM AND APPARATUS. The hemispherical bodies 36 and 38 were the largest which could be fitted within the confines of the existing heads.

Figure 3:
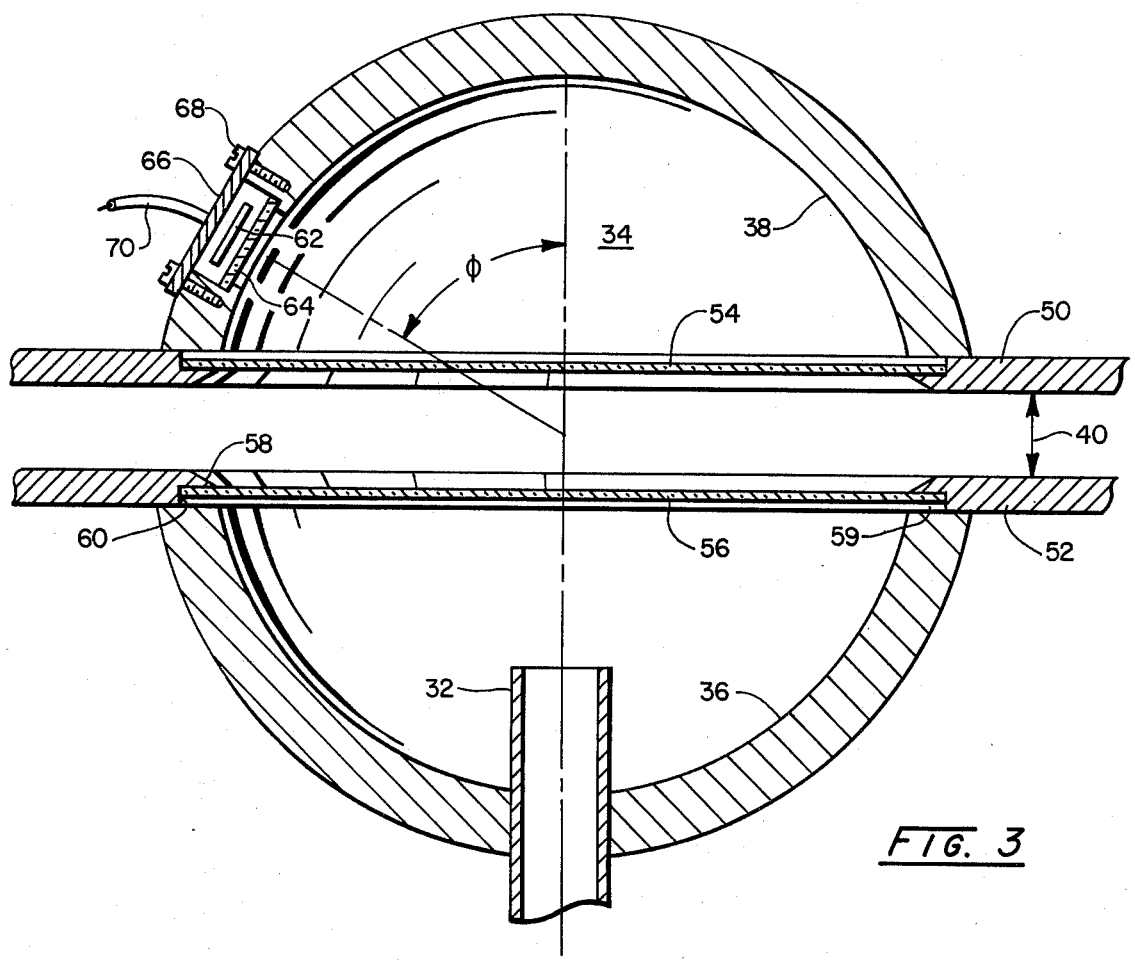
FIG. 3 is an enlargement of a portion of FIG. 1 showing more detail.

As shown by FIG. 3, the pass gap 40 is defined by a pair of face plates 50 and 52. The openings in the face plates are covered by glass windows 54 and 56. The windows are recessed below the outside surfaces of the face plates toward pass gap 40 and the recessed openings are beveled as indicated at 58. The windows in the constructed embodiment were 3/32 inch thick and were simply cemented into stepped openings as at 59 slightly larger than the beveled openings. The glass windows are designed to be kept clean on the outside by an air wipe arrangement (not shown) which is fully described in the copending application of Juan H. Crawford, Ser. No. 693,492, filed June 7, 1976 for FLUID SYSTEM AND METHOD.

FIG. 1 shows generally a detector 42 on the side of the sheet 10 opposite the radiation source arrangement 18 and light pipe 32. Detector 42 detects both the projected radiation from light pipe 32 which is transmitted by the sheet 10 and radiation reflected from the reflective bodies 36 and 38. The output of detector 42 is fed via line 70 to a conventional ratio analyzer 72. Analyzer 72 is the signal processing portion of the detecting means including detector 42. Analyzer 72 computes a function of the ratio of the signals detected at the absorption and reference wavelengths to produce an output response on line 74 indicative of the measured property, in this case the moisture content, of sheet 10. This response may be registered by any suitable output device 76 such as a percent moisture meter.

Detector 42 is shown in more detail in FIG. 3. The detector element 62 is located behind a band pass filter 64 adapted to block out most of the ambient radiation entering cavity 34 through the pass gap between face plates 50 and 52 and window 54. The filter 64, however, does not substantially attenuate the wavelengths passed by filter 24 and 26 through light pipe 32 and thereby projected onto the sheet 10. The filter 64 is a circular disc which sits on a ledge at the bottom of a shallow bored passage extending from the outside of body 38. The hole through the inner, mirrored surface of body 38 is smaller than the filter, thus forming the ledge on which the filter 62 is seated. The detector element 62 has an effectively wide field of view through the filter 62 and the opening into cavity 34. The axis of view for the detector element passes through the center of the pass gap. The axis of light pipe 32 also passes through the center of the cavity 34. The angle between the light pipe axis and the detector's viewing axis is shown in FIG. 3 as the angle $\phi$.

In the embodiment of the invention which has been constructed the angle $\phi$ was 50°. By selecting the angle $\phi$ it is possible to select the relative quantities, of the radiation projected onto sheet 10 and transmitted by the sheet, and the radiation reflected from the mirrored inner surfaces of reflective bodies 36 and 38.

Figure 2:
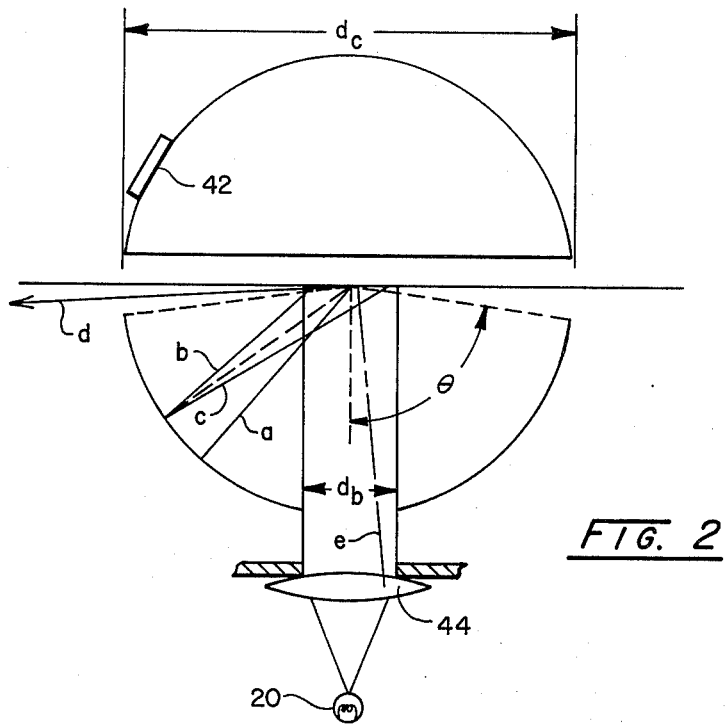
FIG. 2 is a sketch generally resembling a portion of FIG. 1 and illustrating certain geometrical relations therein.

With reference to FIG. 2, the proper action of the cavity 34 is maintained by properly choosing the ratio of the projected spot or source beam diameter $d_b$ to the diameter $d_c$ of the spherical cavity and by redirecting substantial amounts of scattered radiation back to the close vicinity of the initial source beam impinging on the sheet by using a spherical mirror. This spherical mirror is, of course, specularly reflecting and should be distinguished from an integrating sphere. For this technique to function properly the surface must be specularly reflecting and should stimulate a partial spherical surface.

If the ratio of the beam diameter ($d_b$) to the diameter $d_c$ of the cavity sphere is small, a substantial amount of the diffusely reflected radiation from the sheet will be reflected by the spherical surface back to the original beam location. For example, when the paper is placed at the middle of the pass gap, the reflected beam $a$ originating from the center of the sphere will trace back the same path after it is reflected from the specular spherical surface. The beam $b$ which originates from one end of the measured area will follow the path $c$ after reflection from the spherical surface, still remaining in the original measured area of the sheet. The only leakage of the light beam is represented by the paths $d$ and $e$ which do not intersect with the reflecting surface. The amount of leakage can be easily calculated from solid angle and angular reflection patterns. The percentage of leakage through the source aperture is approximated from $$2 \times 100 \frac{\pi d_b^2}{2\pi d_c^2} = 100 \left(\frac{d_b}{d_c}\right)^2$$

Therefore, if $$\frac{d_b}{d_c} \leq 0.3,$$

then the leakage through the source aperture is less than 1%. The factor 2 on the left-hand side of the equation is the result of the assumption of Lambert (cosine law) reflection. The leakage through the gap (represented by the beam $d$) can be calculated from $$\frac{\int_\theta^{\frac{\pi}{2}} \sin\theta\cos\theta d\theta}{\int_0^{\frac{\pi}{2}} \sin\theta\cos\theta d\theta} = \cos^2\theta$$

where $\theta$ is the angle as shown in FIG. 2. If the ratio of the gap between the two reflecting surfaces to the diameter of the sphere is $r$, then $$r = \cos\theta$$

Thus, if the gap is 1.0 inches and the diameter of the sphere is 5 inches, then the leakage through the side will be $$\left(\frac{1.0}{5}\right)^2 = 0.04 = 4\%$$

It is noted that the 1.0 inch gap here includes the thickness of the face plates 50 and 52, since radiation impinging on the face plates is substantially lost. There will be some additional loss of radiation due to the windows covering the mirrors and the loss at the mirror surface.

The expected performance of this arrangement can be estimated by recognizing the fact that the interaction process will be very similar to the case where the sheet is tightly sandwiched between two flat mirrors or diffusers. Thus the signal generated in the detector 42 mounted as shown in FIG. 2 is $$T = \frac{\alpha T_o}{(1 - R_o R_g)(1 - RR_g)}$$

where $\alpha$ is a proportionality constant $T_o$ and $R_o$ are the transmittance and reflectance of the sheet with no reflectors, $R_g$ is the effective reflectivity of the mirrors which is (1-losses) described above, and $$R = R_o + \frac{R_g T_o^2}{1 - R_o R_g}.$$

The effective reflectivity $R_g$ of the mirrors (reflective bodies 36 and 38) is typically in the range of about 0.5 to 0.8, and ordinarily for best results it will be around 0.65 or 0.70. Taking into account the losses and the desirable size of the bodies 36 and 38 it may be desired to make the surface reflectance of the bodies per se fairly high, perhaps in the range of 0.7 to 0.9. The higher the reflectance, the smaller the cavity which can be used while still achieving the value of $R_g$ needed to obtain satisfactory compensation for bone dry weight and composition variations.

While the foregoing specification and the drawings describe and illustrate typical methods and apparatus for practicing the invention, it is to be understood that such description and illustration is meant to be illustrative only and not restrictive, since obviously many modifications of the procedures and apparatus described herein can be made without departing from the spirit and scope of the invention. For example, as suggested in FIG. 2, a lens 44 rather than the light pipe 32 may be used to project the spot of radiation onto the sheet. Instead of using a detector 42 at the periphery of the cavity and at angle $\phi$, one may use a detector mounted closer to the center of the cavity and in line with the projected beam, for example, a detector arranged in a manner similar to that described in the Williams et al application supra, provided the proper balance of transmitted and reflected radiation is detected.

What is claimed is:

1. The method of measuring a property such as moisture content in a sheet of material such as paper that both absorbs and strongly scatters infrared radiation, comprising the steps of passing the sheet through the central region of a substantially spherical cavity formed between a pair of concave mirror-surfaced, specularly reflecting bodies that are spaced apart to form a pass gap of sufficient width to allow substantially free movement of the sheet therethrough while substantially enclosing a first portion of the sheet on both sides, projecting onto one side of the sheet in the center of the cavity a spot of infrared radiation to illuminate a second portion of the sheet included within and substantially smaller than the enclosed first portion so that infrared radiation scattered or transmitted by the second portion will be reflected from the mirror-surfaced bodies and directed back to the second portion substantially within the area of the sheet defined by the spot, the relative sizes of the first and second portions in relation to the width of the pass gap determining the relative quantities of radiation being retained in the cavity and escaping through the pass gap, and detecting on the opposite side of the sheet relative quantities of both the projected radiation transmitted by the sheet and radiation reflected from the reflective bodies so as to produce an output response indicative of said property, said relative quantities of retained and escaping radiation and detected transmitted and reflected radiation being selected to make said response substantially independent of changes in another property affecting the scattering power of the sheet material, such as the bone-dry weight or composition of paper.

2. A method as in claim 1 wherein the radiation is projected along a diameter of the spherical cavity.

3. A method as in claim 2 comprising detecting the radiation from a location at an angle $\phi$ from the diameter along which the radiation is projected, said angle determining the relative detected quantities of projected transmitted radiation and radiation reflected by the bodies.

4. A method as in claim 3 wherein the diameter is substantially normal to the sheet.

5. A method as in claim 3 wherein the angle $\phi$ has its apex substantially at the center of the cavity, and is about 50°.

6. A method as in claim 1 wherein the diameter of the cavity is on the order of about 5–10 times the size of the projected spot.

7. A method as in claim 1 wherein the effective reflectivity $R_g$ of the reflective bodies is about 0.5 to 0.8.

8. A apparatus for measuring a property such as moisture content in a sheet of material such as paper that both absorbs and strongly scatters infrared radiation, comprising a pair of concave mirror-surfaced, specularly reflecting bodies forming a substantially spherical cavity therebetween and spaced apart to form a pass gap of sufficient width to allow substantially free movement of the sheet between the bodies and through the central region of the cavity while substantially enclosing a first portion of the sheet on both sides, means for projecting onto one side of the sheet in the center of the cavity a spot of infrared radiation to illuminate a second portion of the sheet included within and substantially smaller than the enclosed first portion so that infrared radiation scattered or transmitted by the second portion will be reflected from the mirror-surfaced bodies and directed back to the second portion substantially within the area of the sheet defined by the spot, the relative sizes of the first and second portions in relation to the width of the pass gap determining the relative quantities of radiation being retained in the cavity and escaping through the pass gap, and means for detecting on the opposite side of the sheet relative quantities of both the projected radiation transmitted by the sheet and radiation reflected from the reflective bodies so as to produce an output response indicative of said property, said relative quantities of retained and escaping radiation and detected transmitted and reflected radiation being selected to make said response substantially independent of changes in another property affecting the scattering power of the sheet material, such as the bone-dry weight of composition of paper.

9. Apparatus as in claim 8 wherein the projecting means projects the radiation along a diameter of the spherical cavity.

10. Apparatus as in claim 9 wherein the detecting means comprises a radiation detector element mounted at an angle $\phi$ from the diameter along which the radiation is projected, said angle determining the relative detected quantities of projected transmitted radiation and radiation reflected by the bodies.

11. Apparatus as in claim 10 wherein the projecting means projects radiation along a diameter of the cavity substantially normal to the sheet.

12. Apparatus as in claim 10 wherein the angle $\phi$ has its apex substantially at the center of the cavity and is about 50°.

13. Apparatus as in claim 8 wherein the diameter of the cavity is on the order of about 5–10 times the size of the projected spot.

14. Apparatus as in claim 8 wherein the effective reflectivity of the reflective bodies is about 0.5 to 0.8.

* * * * *